United States Patent
Braun et al.

(10) Patent No.: US 9,333,162 B2
(45) Date of Patent: May 10, 2016

(54) THICKENING POLYMER REDUCING THE STICKINESS OF GLYCERINE-BASED COSMETIC FORMULAS

(71) Applicants: Olivier Braun, St Just St Rambert (FR); Paul Mallo, Croissy-sur-Seine (FR)

(72) Inventors: Olivier Braun, St Just St Rambert (FR); Paul Mallo, Croissy-sur-Seine (FR)

(73) Assignee: SOCIETE D'EXPLOITATION DE PRODUITS POUR LES INDUSTRIES CHIMIQUES SEPPIC, Paris (FR)

(*) Notice: Subject to any disclaimer, the term of this patent is extended or adjusted under 35 U.S.C. 154(b) by 49 days.

(21) Appl. No.: 14/373,742

(22) PCT Filed: Jan. 16, 2013

(86) PCT No.: PCT/FR2013/050095
§ 371 (c)(1),
(2) Date: Jul. 22, 2014

(87) PCT Pub. No.: WO2013/110880
PCT Pub. Date: Aug. 1, 2013

(65) Prior Publication Data
US 2014/0350126 A1 Nov. 27, 2014

(30) Foreign Application Priority Data
Jan. 25, 2012 (FR) ...................... 12 50701

(51) Int. Cl.
| | | |
|---|---|---|
| A61K 47/32 | (2006.01) | |
| A61K 8/81 | (2006.01) | |
| A61Q 1/14 | (2006.01) | |
| C08F 14/18 | (2006.01) | |
| A61Q 19/00 | (2006.01) | |
| C08F 283/01 | (2006.01) | |

(52) U.S. Cl.
CPC ............... *A61K 8/8158* (2013.01); *A61K 47/32* (2013.01); *A61Q 1/14* (2013.01); *A61Q 19/00* (2013.01); *C08F 14/185* (2013.01); *C08F 283/01* (2013.01); *A61K 2800/48* (2013.01)

(58) Field of Classification Search
CPC .................................................. C08F 214/182
See application file for complete search history.

(56) References Cited

U.S. PATENT DOCUMENTS

| | | | |
|---|---|---|---|
| 2,798,053 A | 7/1957 | Harold et al. | |
| 5,368,850 A | 11/1994 | Cauwet et al. | |
| 5,373,044 A | 12/1994 | Adams et al. | |
| 5,410,005 A * | 4/1995 | Nemoto | G03F 7/091 430/273.1 |
| 5,458,881 A | 10/1995 | Berger et al. | |
| 5,549,681 A | 8/1996 | Segmuller et al. | |
| 5,670,471 A | 9/1997 | Amalric et al. | |
| 5,888,482 A | 3/1999 | Amalric et al. | |
| 5,958,431 A | 9/1999 | Brancq et al. | |
| 6,437,068 B2 | 8/2002 | Loffler et al. | |
| 6,645,476 B1 | 11/2003 | Morschhauser et al. | |
| 2008/0124524 A1* | 5/2008 | Yoshimura | G06F 7/091 428/195.1 |
| 2011/0040018 A1* | 2/2011 | Mock | C09D 133/26 524/502 |

FOREIGN PATENT DOCUMENTS

| | | |
|---|---|---|
| DE | 195 23 596 A1 | 1/1997 |
| EP | 0 301 532 A2 | 2/1989 |
| EP | 0 603 019 A1 | 6/1994 |
| EP | 0 684 024 A2 | 11/1995 |
| EP | 0 816 403 A2 | 1/1998 |
| EP | 1 069 142 A1 | 1/2001 |
| EP | 1 116 733 A1 | 7/2001 |
| EP | 1 757 627 A1 | 2/2007 |
| FR | 2 734 496 A1 | 11/1996 |
| JP | 2005-162826 * | 6/2005 |
| JP | 2005/162829 A | 6/2005 |
| WO | 92/06778 A1 | 4/1992 |
| WO | 92/21316 A1 | 12/1992 |
| WO | 92/21318 A1 | 12/1992 |
| WO | 93/07856 A1 | 4/1993 |
| WO | 93/08204 A1 | 4/1993 |
| WO | 94/27561 A1 | 12/1994 |
| WO | 95/04592 A1 | 2/1995 |

(Continued)

OTHER PUBLICATIONS

International Search Report, dated Mar. 13, 2013, from corresponding PCT application.
FR Search Report, dated Jul. 24, 2012, from corresponding FR application.

*Primary Examiner* — Brian Gulledge
(74) *Attorney, Agent, or Firm* — Young & Thompson

(57) ABSTRACT

A linear, branched or cross-linked anionic polyelectrolyte, resulting from the polymerisation, for 100 molar percentage: a) 50% to 99% of monomeric units including a strong, free and partially or completely salified acid function ; b) 1% to 50% of a monomeric units of formula (I): $CH_2=CH(R1)-C(=O)-O-(CH2)n-CF3$ (I), wherein R1 represents H or $CH_3$, and n is 1, 2 or 3; c) optionally greater than 0% to 5% of monomeric units of formula (II): $R2-C(=O)-O-[(CH2-CH(R4)-O]m-R3$ (II), wherein m is 0 to 50, R2 represents an unsaturated aliphatic monovalent radical with 2 to 4 carbon atoms, R4 represents H, $CH_3$ or $CH_3CH_2$ and R3 represents a linear or branched, saturated or unsaturated hydrocarbon aliphatic radical with 8 to 30 carbon atoms, and d) optionally greater than 0% to 5% of at least one monomer with diethylenic or polyethylenic cross-linking. The use thereof as a thickener in topical compositions.

16 Claims, No Drawings

(56) References Cited

FOREIGN PATENT DOCUMENTS

| WO | 95/13863 A1 | 5/1995 |
| WO | 96/37285 A1 | 11/1996 |
| WO | 98/09611 A1 | 3/1998 |
| WO | 98/22207 A1 | 5/1998 |
| WO | 98/47610 A1 | 10/1998 |
| WO | 2009/143194 A | 11/2009 |
| WO | 2011030044 A1 | 3/2011 |

* cited by examiner

THICKENING POLYMER REDUCING THE STICKINESS OF GLYCERINE-BASED COSMETIC FORMULAS

The invention relates to novel thickeners and also to their cosmetic and pharmaceutical use.

It is well known to thicken aqueous phases intended for cosmetic, dermo-pharmaceutical or pharmaceutical uses by introducing therein synthetic or natural hydrophilic polymers. Natural polymers such as xanthan or guar gums are quite widely used, but have the standard drawbacks of natural products (fluctuating quality and price). This is why synthetic thickening polymers are widely used for increasing the viscosity of creams, emulsions and various topical solutions. They are either in powder form or in liquid form. In the latter option, the polymer is prepared by inverse emulsion polymerization using surfactants and the resulting liquid form is a water-in-oil emulsion containing the polymer, this emulsion commonly being known as an inverse latex.

The thickening polymers in powder form that are the most commonly known are polymers based on acrylic acid or copolymers based on acrylic acid and esters thereof, for instance the polymers sold under the names Carbopol™ and Pemulen™ and which are described especially in U.S. Pat. No. 5,373,044 and U.S. Pat. No. 2,798,053 and also in European patent EP 0 301 532, or alternatively homopolymers or copolymers based on 2-acrylamido-2-methylpropane-sulfonic acid sold under the name Aristoflex™ and which are described especially in European patents EP 0 816 403, EP 1 116 733 and EP 1 069 142 or Sepimax™ Zen described in international patent application WO 2011/030 044. These polymer powders are obtained by precipitating polymerization in an organic solvent such as benzene, ethyl acetate, cyclohexane or tert-butanol.

Inverse latices, for example those sold under the names Sepigel™ 305, Simulgel™ 600, Simulgel™ EG, Simulgel™ EPG, Simulgel™ NS, Simulgel™ A, Sepiplus™ 400, Sepiplus™ 250 and Sepiplus™ 265, obtained by inverse emulsion polymerization, are more easily manipulable and disperse very rapidly in water. They develop appreciably high thickening performance qualities, which are probably the consequence of the process for preparing them, a dispersed-phase polymerization reaction, which leads to polymers of very high molecular weights.

The abovementioned polymers are essentially intended for thickening the aqueous phases of cosmetic, dermopharmaceutical or pharmaceutical topical formulations.

Now, certain formulations, more particularly those intended for skincare, also contain relatively large amounts of glycerol, typically between 5% and 10% by mass, for increasing their moisturizing power. However, since the presence of glycerol therein also considerably increases their tacky effect, formulators add thereto silicone oils to limit or eliminate this tacky effect.

However, the addition of silicone oils complicates the preparation of these formulations. Furthermore, the presence of silicone oils in formulations, which are intended to be in direct contact with the skin, is poorly appreciated by the end consumer. The cosmetic industry thus attempts to limit the use thereof.

The inventors have thus sought to develop novel thickening polymers that are effective over a wide pH range, and that are capable of reducing or eliminating the tacky effect induced by the presence of glycerol, without it being necessary to add intermediary compounds such as silicone derivatives. They have found that polymer powders derived from the precipitating polymerization of fluoro monomers and of a monomer bearing a strong acid function solve these problems.

Accordingly, according to a first aspect, a subject of the invention is a linear, branched or crosslinked anionic polyelectrolyte derived from the polymerization, per 100 mol %:

a) of a mole proportion of greater than or equal to 50% and less than or equal to 99% of monomer units derived from a monomer comprising a free, partially salified or totally salified strong acid function;

b) of a mole proportion of greater than or equal to 1% and less than or equal to 50% of a monomer of formula (I):

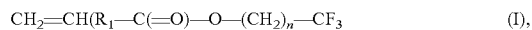

$$CH_2=CH(R_1)-C(=O)-O-(CH_2)_n-CF_3 \qquad (I),$$

in which formula (I) the radical $R_1$ represents a hydrogen atom or a methyl radical, and n represents an integer equal to 1, 2 or 3;

c) optionally, of a mole proportion of greater than 0% and less than or equal to 5 mol %, of monomer units derived from at least one monomer of formula (II):

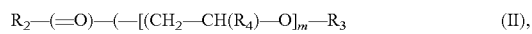

$$R_2-(=O)-(-[(CH_2-CH(R_4)-O]_m-R_3 \qquad (II),$$

in which formula (II) m represents a number greater than or equal to 0 and less than or equal to 50, $R_2$ represents an unsaturated aliphatic monovalent radical comprising from 2 to 4 carbon atoms, $R_4$ represents a hydrogen atom, a methyl radical or an ethyl radical and $R_3$ represents a linear or branched, saturated or unsaturated hydrocarbon-based aliphatic radical comprising from 8 to 30 carbon atoms, and d) optionally of a mole proportion of greater than 0% and less than or equal to 5% of at least one diethylenic or polyethylenic crosslinking monomer.

The term "branched polyelectrolyte" denotes a nonlinear polyelectrolyte which bears pendent chains so as to obtain, when it is dissolved in water, a high state of entanglement leading to very high viscosities, at low rate gradients.

The term "crosslinked polyelectrolyte" denotes a nonlinear polyelectrolyte which is in the form of a water-insoluble but water-swellable three-dimensional network and thus leading to the production of a chemical gel.

The polyelectrolyte obtained via the process according to the invention may comprise crosslinked units and/or branched units.

According to a particular aspect of the present invention, in formula (I) as defined above, n is equal to 1.

According to another particular aspect of the present invention, in formula (I) as defined above, $R_1$ represents a methyl radical.

The term "monomer comprising a free, partially salified or totally salified strong acid function" especially denotes monomers bearing a sulfonic function ($—SO_3H$).

According to a particular aspect, said at least one monomer comprising a free, partially salified or totally salified strong acid function is free, partially salified or totally salified 2-methyl-2-[(1-oxo-2-propenyl)amino]-1-propanesulfonic acid.

The term "partially salified or totally salified strong acid function" denotes, in the context of the present invention, a partially or totally salified acid function especially in the form of an alkali metal salt, for instance the sodium salt or the potassium salt or in the form of an ammonium salt.

According to another particular aspect, a subject of the invention is an anionic polyelectrolyte as defined previously, in which said at least one monomer comprising a partially or totally salified strong acid function is 2-methyl-2-[(1-oxo-2-propenyl)amino]-1-propanesulfonic acid, which is partially or totally salified in ammonium salt form.

According to another particular aspect, the linear, branched or crosslinked polyelectrolyte is characterized in that the mole proportion of monomer units derived from the monomer comprising a free, partially salified or totally salified strong acid function is less than or equal to 95%.

According to another particular aspect of the present invention, the polyelectrolyte as defined above is characterized in that the mole proportion of monomer units derived from the monomer comprising a free, partially salified or totally salified strong acid function is greater than or equal to 60%.

In formula (II) as defined previously, the divalent radical:

$$-[(CH_2-CH(R_4)-O)]_m-$$

especially represents:
- either a chain composed solely of ethoxyl groups ($R_4$=H; n>0),
- or a chain composed solely of propoxyl groups ($R^4$=CH$_3$, n>0);
- or a chain composed solely of butoxyl groups ($R_4$=C$_2$H$_5$; n>0),
- or a chain composed of at least two different groups chosen from ethoxyl, propoxyl and/or butoxyl groups.

When this chain is composed of different groups, they are distributed along this chain, in a block or random manner.

The term "saturated or unsaturated linear hydrocarbon-based aliphatic radical comprising from 8 to 30 carbon atoms" more particularly denotes for $R_3$, in formula (II) as defined previously:
- either a radical derived from linear primary alcohols, for instance those derived from octyl, pelargonyl, decyl, undecyl, undecenyl, lauryl, tridecyl, myristyl, pentadecyl, cetyl, heptadecyl, stearyl, oleyl, linoleyl, nonadecyl, arachidyl, behenyl, erucyl or 1-triacontanyl alcohol. They may then be octyl, nonyl, decyl, undecyl, 10-undecenyl, dodecyl, tridecyl, tetradecyl, pentadecyl, hexadecyl, heptadecyl, octadecyl, 9-octadecenyl, 10,12-octadecadienyl, 13-docosenyl or triacontanyl radicals;
- or a radical derived from Guerbet alcohols, which are branched 1-alkanols corresponding to the general formula:

$$CH_3-(CH_2)_p-CH[CH_3-(CH_2)_{p-2}]-CH_2OH,$$

in which p represents an integer between 2 and 14, for instance 2-ethylhexyl, 2-propylheptyl, 2-butyloctyl, 2-pentylnonyl, 2-hexyldecyl or 2-octyldodecyl radicals;
- or a radical derived from isoalkanols corresponding to the general formula:

$$CH_3-CH(CH_3-(CH_2)_m-CH_2OH,$$

in which m represents an integer between 2 and 26, for instance 4-methylpentyl, 5-methylhexyl, 6-methylheptyl, 15-methylpentadecyl or 16-methylheptadecyl radicals;
- or 2-hexyloctyl, 2-octyldecyl or 2-hexyldodecyl radicals.

The term "linear or branched, saturated or unsaturated hydrocarbon-based aliphatic radical comprising from 8 to 30 carbon atoms" more particularly denotes for $R_3$, in formula (II) as defined previously, an alkyl radical comprising from 12 to 22 carbon atoms.

In formula (II) as defined previously, m more particularly represents a number greater than or equal to 0 and less than or equal to 25.

In formula (II) as defined previously, $R_2$ more particularly represents the vinyl radical (CH$_2$=CH—) or the isopropenyl radical [CH$_2$=C(CH$_3$)—].

According to a more particular aspect of the present invention, said monomer of formula (II) as defined previously is chosen from:
- pentacosaethoxylated behenyl methacrylate, compound of formula (II) as defined previously, in which $R_3$ represents the docosanyl radical, $R_2$ represents the isopropenyl radical, $R_4$ represents a hydrogen atom and n is equal to 25;
- tetraethoxylated lauryl acrylate, compound corresponding to formula (II) as defined previously, in which $R_3$ represents the dodecyl radical, $R_2$ represents the vinyl radical, $R_4$ represents a hydrogen atom and n is equal to 4,
- eicosaethoxylated stearyl methacrylate, compound of formula (II) as defined previously, in which $R_3$ represents the stearyl radical, $R_2$ represents the isopropenyl radical, $R_4$ represents a hydrogen atom and n is equal to 20;
- tetraethoxylated lauryl methacrylate, compound corresponding to formula (I) as defined previously, in which $R_3$ represents the dodecyl radical, $R_2$ represents the isoprenyl radical, $R_4$ represents a hydrogen atom and n is equal to 4, or
- stearyl methacrylate, compound of formula (II) as defined previously, in which $R_3$ represents the stearyl radical, $R_2$ represents the isopropenyl radical, $R_4$ represents a hydrogen atom and n is equal to 0.

According to a particular aspect, a subject of the invention is more particularly a polyelectrolyte as defined previously, derived from the polymerization, per 100 mol %:
a) of a mole proportion of greater than or equal to 60% and less than or equal to 90% of monomer units derived from a monomer comprising a free, partially salified or totally salified strong acid function;
b) of a mole proportion of greater than or equal to 9% and less than or equal to 35% of monomer units derived from a monomer of formula (I); and
c) of a mole proportion of greater than or equal to 1% and less than or equal to 5% of monomer units derived from the compound of formula (II).

According to another particular aspect of the present invention, the polyelectrolyte as defined above is crosslinked.

According to the latter aspect, said at least one diethylenic or polyethylenic crosslinking monomer is chosen especially from diallyloxyacetic acid or a salt thereof such as the sodium salt thereof, triallylamine, trimethylolpropane triacrylate, ethylene glycol dimethacrylate, diethylene glycol diacrylate, diallylurea or methylenebis(acrylamide) or a mixture of several of these compounds.

According to a most particular aspect of the present invention, the crosslinking agent used is methylene-bis(acrylamide) or trimethylolpropane triacrylate (TMPTA).

The crosslinking agent is then generally used in a mole proportion, expressed relatively to the monomers used, of from 0.005 mol % to 5 mol % and more particularly from 0.5 mol % to 2 mol %.

According to a particular aspect, a subject of the invention is more particularly a polyelectrolyte as defined previously, derived from the polymerization, per 100 mol %:
a) of a mole proportion of greater than or equal to 60% and less than or equal to 90% of monomer units derived from a monomer comprising a free, partially salified or totally salified strong acid function,
b) of a mole proportion of greater than or equal to 9.99% and less than or equal to 35% of monomer units derived from a monomer of formula (I); and
d) of a mole proportion of greater than or equal to 0.01% and less than or equal to 5 mol % of monomer units derived from at least one diethylenic or polyethylenic crosslinking monomer.

According to another particular aspect, a subject of the invention is more particularly a polyelectrolyte as defined previously, derived from the polymerization, per 100 mol %:

a) of a mole proportion of greater than or equal to 60% and less than or equal to 90% of monomer units derived from a monomer comprising a free, partially salified or totally salified strong acid function,
b) of a mole proportion of greater than or equal to 9.99% and less than or equal to 35% of monomer units derived from a monomer of formula (I);
c) of a mole proportion of greater than or equal to 0.005% and less than or equal to 5 mol % of monomer units derived from the compound of formula (II); and
d) of a mole proportion of greater than or equal to 0.005% and less than or equal to 5 mol % of monomer units derived from at least one diethylenic or polyethylenic crosslinking monomer.

A subject of the invention is most particularly a crosslinked anionic polyelectrolyte derived from the polymerization, per 100 mol %:
a) of a mole proportion of greater than or equal to 60% and less than or equal to 90% of monomer units derived from 2-methyl-2-[(1-oxo-2-propenyl)amino]-1-propanesulfonic acid, which is free, partially salified or totally salified in sodium salt or ammonium salt form;
b) of a mole proportion of greater than or equal to 9% and less than or equal to 35% of monomer units derived from 2,2,2-trifluoroethyl methacrylate;
c) of a mole proportion of greater than or equal to 0.5 mol % and less than or equal to 2 mol % of monomer units derived from stearyl methacrylate, and
d) of a mole proportion of greater than or equal to 0.5% and less than or equal to 3% of trimethylol triacrylate.

A subject of the invention is also a process for preparing the polyelectrolyte as defined previously, characterized in that it comprises:
a step a) of preparation of a reaction mixture comprising, in the desired mole proportions and in a solvent (S), the monomer(s) comprising a free, partially salified or totally salified strong acid function, the monomer(s) of formula (I); if necessary or if desired, the monomer units derived from the compound of formula (II); and if necessary or if desired, the diethylenic or polyethylenic crosslinking monomer(s), said solvent (S) being:
either a ketone of formula (III):

$(R_5)(R_6)C=O$      (III), in which $R_5$ and $R_6$, which may be identical or different, represent, independently of each other, a methyl radical, an ethyl radical, an isopropyl radical or an isobutyl radical;
or a mixture consisting of, per 100 mol %:
water in a proportion of greater than 0 mol % and less than or equal to 25 mol %; and
a ketone of formula (III) as defined above, in a proportion of greater than or equal to 75 mol % and less than 100%;
or tert-butanol;
a step b) during which the polymerization reaction is initiated by introducing into said reaction mixture prepared in step a), a free-radical initiator, and is then left to proceed until finished, to obtain a precipitate of said polyelectrolyte.

According to another particular aspect of the present invention, in step b) of the process as defined previously, the polymerization reaction is initiated at a temperature of greater than or equal to 50° C. using a radical initiator that produces radicals by homolysis, such as dilauroyl peroxide, cyclohexyl peroxide dicarbonate, isopropyl peroxide dicarbonate, azobis (isobutyronitrile) or azo derivatives.

According to another particular aspect of the present invention, in step b) of the process as defined previously, the polymerization reaction is initiated with a redox couple such as a redox couple that generates hydrogenosulfite ions ($HSO_3$), such as the cumene hydroperoxide-sodium metabisulfite ($Na_2S_2O_5$) couple or the cumene hydroperoxide-thionyl chloride ($SOCl_2$) couple at a temperature of less than or equal to 20° C., if desired accompanied by a polymerization coinitiator, for instance azobis(isobutyronitrile), dilauryl peroxide, cyclohexyl peroxide dicarbonate, isopropyl peroxide dicarbonate or sodium persulfate, and is then conducted virtually adiabatically.

According to another particular aspect of the present invention, in step b) of the process as defined previously, the polymerization reaction is initiated at a temperature of greater than or equal to 50° C. using a radical initiator that produces radicals by homolysis, such as dilauroyl peroxide, azobis (isobutyronitrile) or azo derivatives.

The process as defined above may also comprise:
a step c) of isolation of said precipitate obtained in step b) by separation from said solvent (S), and then if desired or if necessary,
a step d) of drying said precipitate resulting from step c.

According to another particular aspect of the present invention, in step c) of the process as defined previously, the separation of the precipitate obtained from said organic solvent is performed by filtration.

According to another particular aspect, a subject of the invention is a process as defined above, in which said solvent (S) is either acetone or a water-acetone mixture in a water/acetone mole ratio of greater than 0 and less than or equal to 5/95, or tert-butanol.

A subject of the invention is also the use of the anionic polyelectrolyte as defined previously, as a thickener and/or a stabilizer and/or as an emulsifier for a cosmetic, dermopharmceutical or pharmaceutical topical composition.

A topical composition according to the invention, intended to be applied to the skin or mucous membranes of man or animals, may consist of a topical emulsion comprising at least one aqueous phase and at least one oil phase. This topical emulsion may be an oil-in-water (O/W), water-in-oil (W/O), oil-in-water-in-oil (O/W/O) or water-in-oil-in-water (W/O/W) emulsion. The oil phase of the topical emulsion may consist of a mixture of one or more oils.

A topical composition according to the invention may be intended for cosmetic use or may be used for preparing a medicament for treating skin, scalp and mucous membrane diseases. In the latter case, the topical composition then comprises an active principle which may consist, for example, of an antiinflammatory agent, a muscle relaxant, an antifungal agent, an antibacterial agent or an antidandruff agent.

When the topical composition is used as a cosmetic composition intended to be applied to the skin, the scalp or mucous membranes, it may or may not comprise an active principle, for example a moisturizer, a tanning agent, a sunscreen, an antiwrinkle agent, a slimming agent, a free-radical scavenger, an antiacne agent, an antifungal agent or an antidandruff agent.

The topical composition according to the invention usually comprises between 0.1% and 10% by mass and more particularly from 1% to 5% by mass of anionic polyelectrolyte as defined previously.

According to a particular aspect, the topical composition as defined above also comprises from 1% by mass to 10% by mass of glycerol.

The pH of the topical composition is preferably greater than or equal to 3.

The topical composition may also comprise compounds conventionally included in compositions of this type, for example fragrances, preserving agents, dyes, pigments, sunscreens, active ingredients, emollients or surfactants.

The anionic polyelectrolyte according to the invention is an advantageous substitute for the thickeners sold under the names Sepigel™ 305, Sepigel™ 501, Simulgel™ EG, Simulgel™ EPG, Simulgel™ NS, Simulgel™ 600, Simulgel™ A, Sepiplus™ 265, Sepiplus™ 250, Sepiplus™ 400 or Sepinov™ EMT 10 or Sepimax™ Zen by the Applicant, since it also has good compatibility with the other excipients used for the preparation of formulations such as milks, lotions, creams, soaps, baths, balms, shampoos or hair conditioners. It may also be used with said products Sepigel™ or Simulgel™, Sepiplus™ and/or Sepinov™ EMT 10.

It is especially compatible with the concentrates described and claimed in international publications WO 92/06778, WO 95/04592, WO 95/13863, WO 96/37285, WO 98/22207, WO 98/47610 or in FR 2 734 496, with the surfactants described in WO 93/08204. It is particularly compatible with Montanov™ 68, Montanov™ 82, Montanov™ 202, Montanov™ L, Montanov™ S, Fluidanov™ 20X or Easynov.

It may also be used for forming cosmetically or physiologically acceptable aqueous gels of acidic pH, such as those described in WO 93/07856; it may also be used in combination with nonionic celluloses, to form, for example, styling gels such as those described in EP 0 684 024, or alternatively in combination with fatty acid esters of sugars, to form hair or skin treatment compositions such as those described in EP 0 603 019, or alternatively in shampoos or hair conditioners as described and claimed in WO 92/21316 or, finally, in combination with an anionic homopolymer such as Carbopol™ to form hair treatment products such as those described in DE 195 23 596.

It is also compatible with N-acylamino acid derivatives, which allows its use in calmative compositions especially for sensitive skin, such as those described or claimed in WO 92/21318, WO 94/27561 or WO 98/09611.

It is also compatible with thickening and/or gelling polymers, such as hydrocolloids of plant or biosynthetic origin, for example xanthan gum, karaya gum, carrageenates, alginates or galactomannans; such as silicates; such as cellulose and derivatives thereof; such as starch and hydrophilic derivatives thereof; such as polyurethanes.

The anionic polyelectrolyte according to the invention furthermore makes it possible to dispense with the use of silicone oil in topical compositions comprising glycerol, since it inhibits the tacky effect induced by this triol.

This is why, according to a final aspect, a subject of the invention is a topical composition comprising between 0.1% and 10% by mass and more particularly from 1% to 5% by mass of the anionic polyelectrolyte as defined previously and from 1% by mass to 10% by mass of glycerol, and characterized in that it is free of silicone oil.

The examples that follow illustrate the invention without, however, limiting it.

EXAMPLE 1

Preparation of an ATBS/TRIFEMA Copolymer Crosslinked with TMPTA 67.7 g of 2-methyl-2-[(1-oxo-2-propenyl)amino]-1-propanesulfonic acid (ATBS) are placed in a reactor maintained at 25° C. with stirring and containing 487.5 g of tert-butanol, followed by addition of ammonia until a pH value of about 6 is reached. After a sufficient time to achieve good homogenization of the solution, it is deoxygenated by sparging with nitrogen, followed by addition of 13.8 g of (2,2,2-trifluoroethyl) methacrylate (TRIFEMA), 12.5 g of deionized water and 2 g of trimethylolpropane triacrylate (TMPTA).

The reaction mixture is stirred for 60 minutes; it is then heated up to a temperature of 60° C. 1 g of dilauroyl peroxide is added thereto. The reaction medium is then stirred again for about 60 minutes and then raised to 80° C. and left at this temperature for 60 minutes. A further 0.33 g of dilauroyl peroxide is added and stirring of the medium is continued at 80° C. for 2 hours.

After cooling, the powder formed during the polymerization is filtered off and dried to obtain the desired product, which is referred to hereinbelow as: Polyelectrolyte 1.

Evaluation of the Thickening Power

Viscosity ($\mu$) of an aqueous dispersion at 2% by mass of Polyelectrolyte 1 [Brookfield RVT, mobile 6, speed: 5 rpm (M6,V5)]: $\mu$=113 000 mPa·s.

Viscosity ($\mu$) of an aqueous dispersion at 2% by mass of Polyelectrolyte 1 and 1% by mass of sodium chloride [Brookfield RVT, (M6,V5)]: $\mu$=2800 mPa·s.

Evaluation of the Tacky Nature of Aqueous Gels Containing Glycerol 250 g of an aqueous gel are prepared by mixing 2.5 g of Polyelectrolyte 1, 25 g of glycerol and 222.5 g of water.

For comparative purposes, 250 g of an aqueous gel are prepared by mixing 6.25 g of Sepigel™ 305, 25 g of glycerol and 218.75 g of water.

By spreading each of the two gels onto a different top surface of the hand, the absence of tacky effect is observed for the gel comprising Polyelectrolyte 1 according to the invention, unlike the gel according to the prior art.

EXAMPLE 2

Preparation of an ATBS/TRIFEMA Copolymer Crosslinked With TMPTA

The process is performed in the same manner as in Example 1, but using only 6.9 g of TRIFEMA and 76.2 g of ATBS. Polyelectrolyte 2 is obtained.

Evaluation of the Thickening Power

Viscosity ($\mu$) of an aqueous dispersion at 2% by mass of Polyelectrolyte 2 [Brookfield RVT, (M6,V5)]: $\mu$=220 000 mPa·s.

Viscosity ($\mu$) of an aqueous dispersion at 2% by mass of Polyelectrolyte 1 and 1% by mass of sodium chloride [Brookfield RVT, (M6,V5)]: $\mu$=12 100 mPa·s.

Evaluation of the Tacky Nature of Aqueous Gels Containing Glycerol 250 g of an aqueous gel are prepared by mixing 2.5 g of Polyelectrolyte 2, 25 g of glycerol and 222.5 g of water.

By spreading this gel onto the top of the hand, the absence of a tacky effect is observed for the gel comprising Polyelectrolyte 2 according to the invention.

EXAMPLE 3

Preparation of an ATBS/TRIFEMA Copolymer Crosslinked With TMPTA

The process is performed in the same manner as in Example 1, but reducing the amount of ATBS to 59.2 g and increasing the amount of TRIFEMA to 20.6 g. Polyelectrolyte 3 is obtained.

Evaluation of the Thickening Power

Viscosity ($\mu$) of an aqueous dispersion containing 2% by mass of Polyelectrolyte 3 [Brookfield RVT, (M6,V5)]: $\mu$=33 800 mPa·s.

Viscosity (μ) of an aqueous dispersion containing 2% by mass of Polyelectrolyte 3 and 1% by mass of sodium chloride [Brookfield RVT, (M6,V5)]: μ=700 mPa·s.

Evaluation of the Tacky Nature of Aqueous Gels Containing Glycerol 250 g of an aqueous gel are prepared by mixing 2.5 g of Polyelectrolyte 3, 25 g of glycerol and 222.5 g of water.

By spreading this gel onto the top of the hand, the absence of a tacky effect is observed for the gel comprising Polyelectrolyte 3 according to the invention.

EXAMPLE 4

Preparation of an ATBS/TRIFEMA Copolymer Crosslinked With TMPTA

Example 1 is repeated, reducing the content TMPTA to 1.21 g. Polyelectrolyte 4 is obtained.

Evaluation of the Thickening Power

Viscosity (μ) of an aqueous dispersion containing 2% by mass of Polyelectrolyte 4 [Brookfield RVT, (M6,V5)]: μ=52 400 mPa·s.

Viscosity (μ) of an aqueous dispersion containing 2% by mass of Polyelectrolyte 4 and 1% by mass of sodium chloride [Brookfield RVT, (M6,V5)]: μ=13 200 mPa·s.

Evaluation of the Tacky Nature of Aqueous Gels Containing Glycerol 250 g of an aqueous gel are prepared by mixing 2.5 g of Polyelectrolyte 4, 25 g of glycerol and 222.5 g of water.

By spreading this gel onto the top of the hand, the absence of a tacky effect is observed for the gel comprising Polyelectrolyte 4 according to the invention.

EXAMPLE 5

Preparation of the ATBS/TRIFEMA Copolymer Crosslinked With TMPTA

Example 1 is repeated, but increasing the amount of TMPTA to 2.4 g. Polyelectrolyte 5 is obtained.

Evaluation of the Thickening Power

Viscosity (μ) of an aqueous dispersion containing 2% by mass of Polyelectrolyte 5 [Brookfield RVT, (M6,V5)]: μ=132 000 mPa·s.

Viscosity (μ) of an aqueous dispersion containing 2% by mass of Polyelectrolyte 5 and 1% by mass of sodium chloride [Brookfield RVT, (M6,V5)]: μ=5300 mPa·s.

Evaluation of the Tacky Nature of Aqueous Gels Containing Glycerol 250 g of an aqueous gel are prepared by mixing 2.5 g of Polyelectrolyte 5, 25 g of glycerol and 222.5 g of water.

By spreading this gel onto the top of the hand, the absence of a tacky effect is observed for the gel comprising Polyelectrolyte 5 according to the invention.

EXAMPLE 6

Preparation of the ATBS/TRIFEMA/SMA Terpolymer Crosslinked With TMPTA

The process is performed in the same manner as for Example 1, but reducing the amount of TMPTA to 1.21 g and in addition adding 1.38 g of stearyl methacrylate (SMA). Polyelectrolyte 6 is obtained.

Evaluation of the Thickening Power

Viscosity (μ) of an aqueous dispersion containing 2% by mass of Polyelectrolyte 6 [Brookfield RVT, (M6,V5)]: μ=130 000 mPa·s.

Viscosity (μ) of an aqueous dispersion containing 2% by mass of Polyelectrolyte 1 and 1% by mass of sodium chloride [Brookfield RVT, (M6,V5)]: μ=11 400 mPa·s.

Evaluation of the Tacky Nature of Aqueous Gels Containing Glycerol 250 g of an aqueous gel are prepared by mixing 2.5 g of Polyelectrolyte 6, 25 g of glycerol and 222.5 g of water.

For comparative purposes, 250 g of an aqueous gel are prepared by mixing 6.25 g of Sepigel™ 305, 25 g of glycerol and 218.75 g of water.

By spreading each of the two gels onto a different surface of the top of the hand, the absence of a tacky effect is observed for the gel comprising Polyelectrolyte 6 according to the invention, unlike the gel according to the prior art.

Examples of Formulations Comprising Glycerol and Free of Silicone Oils Prepared With Polyelectrolytes According to the Invention

EXAMPLE 7

Makeup-Removing Emulsion Containing Sweet Almond Oil

| | |
|---|---|
| Montanov ™ 68: | 5% |
| Sweet almond oil: | 5% |
| Water: | qs 100% |
| Polyelectrolyte 1: | 0.3% |
| Glycerol: | 5% |
| Preserving agent: | 0.2% |
| Fragrance: | 0.3% |

EXAMPLE 8

Emulsion for Atopic-Prone Skin

| | |
|---|---|
| Arlacel ™ P135: | 2.00% |
| Polyelectrolyte 6: | 1.00% |
| Lanol ™ 1688: | 14.00% |
| Primol ™ 352: | 8.00% |
| Glycerol: | 5.00% |
| Water: | qs 100% |
| Magnesium sulfate: | 0.70% |
| Sepicide ™ HB: | 0.30% |
| Sepicide ™ CI: | 0.20% |
| Micropearl ™ M310: | 5.00% |

The definitions of the commercial products used in the examples are as follows:

Montanov™ 68 (cetearyl glucoside) is a self-emulsifying composition as described in WO 92/06778, sold by the company SEPPIC Arlacel™ P135 is PEG-30 dipolyhydroxystearate of HLB 5-6, sold by the company Croda.

Sepicide™ CI, imidazoline urea, is a preserving agent sold by the company SEPPIC.

Lanol™ 1688 is an emollient ester with a non-greasy effect sold by the company SEPPIC.

Sepicide™ HB, which is a mixture of phenoxyethanol, methylparaben, ethylparaben, propylparaben and butyl-paraben, is a preserving agent sold by the company SEPPIC.

Micropearl™ M 310 is an ultrafine powder with a very soft feel and a mattifying action, sold by the company Matsumo.

Primol™ 352 is a mineral oil sold by the company Exxon.

The invention claimed is:

1. A linear, branched or crosslinked anionic polyelectrolyte derived from the polymerization, per 100 mol %:
   a) of a mole proportion of greater than or equal to 50% and less than or equal to 99% of monomer units derived from a monomer comprising a free, partially salified or totally salified strong acid function;
   b) of a mole proportion of greater than or equal to 1% and less than or equal to 50% of a monomer of formula (I):

$$CH_2=CH(R_1)-C(=O)-O-(CH_2)_n-CF_3 \qquad (I);$$

wherein the radical $R_1$ represents a hydrogen atom or a methyl radical, and n represents an integer equal to 1, 2 or 3; and
   c) of a mole proportion of greater than 0% to 5 mol %, of monomer units derived from at least one monomer of formula (II):

$$R_2-C(=O)-O-[(CH_2-CH(R_4)-O]_m-R_3 \qquad (II),$$

wherein m represents a number greater than or equal to 0 and less than or equal to 50, $R_2$ represents an unsaturated aliphatic monovalent radical comprising from 2 to 4 carbon atoms, $R_4$ represents a hydrogen atom, a methyl radical or an ethyl radical, and $R_3$ represents a linear or branched, saturated or unsaturated hydrocarbon-based aliphatic radical comprising from 8 to 30 carbon atoms, and
   d) optionally of a mole proportion of greater than 0% and less than or equal to 5% of at least one diethylenic or polyethylenic crosslinking monomer.

2. The anionic polyelectrolyte as defined in claim 1, wherein, n is equal to 1 and $R_1$ represents a methyl radical.

3. The anionic polyelectrolyte as defined in claim 1, wherein said monomer comprising a free, partially salified or totally salified strong acid function is 2-methyl-2-[(1-oxo-2-propenyl)amino]-1-propanesulfonic acid, which is free, partially salified or totally salified in sodium salt or potassium salt form or in ammonium salt form.

4. The anionic polyelectrolyte as defined in claim 1, wherein said monomer of formula (II) is selected from the group consisting of pentacosaethoxylated behenyl methacrylate, tetraethoxylated lauryl acrylate, eicosaethoxylated stearyl methacrylate, tetraethoxylated lauryl methacrylate and stearyl methacrylate.

5. The anionic polyelectrolyte as defined in claim 1, derived from the polymerization, per 100 mol %:
   a) of a mole proportion of greater than or equal to 60% and less than or equal to 90% of monomer units derived from a monomer comprising a free, partially salified or totally salified strong acid function;
   b) of a mole proportion of greater than or equal to 9% and less than or equal to 35% of monomer units derived from a monomer of formula (I); and
   c) of a mole proportion of greater than or equal to 1% and less than or equal to 5% of monomer units derived from the compound of formula (II).

6. The anionic polyelectrolyte as defined in claim 1, wherein the polyelectrolyte is crosslinked.

7. The anionic polyelectrolyte as defined in claim 6, derived from the polymerization, per 100 mol %:
   a) of a mole proportion of greater than or equal to 60% and less than or equal to 90% of monomer units derived from a monomer comprising a free, partially salified or totally salified strong acid function,
   b) of a mole proportion of greater than or equal to 9.99% and less than or equal to 35% of monomer units derived from a monomer of formula (I); and
   c) of a mole proportion of greater than 0% to 5 mol % of monomer units derived from at least one monomer of formula (II), and
   d) of a mole proportion of greater than or equal to 0.01% and less than or equal to 5 mol % of monomer units derived from at least one diethylenic or polyethylenic crosslinking monomer.

8. The polyelectrolyte as defined in claim 6, derived from the polymerization, per 100 mol %:
   a) of a mole proportion of greater than or equal to 60% and less than or equal to 90% of monomer units derived from a monomer comprising a free, partially salified or totally salified strong acid function,
   b) of a mole proportion of greater than or equal to 9.99% and less than or equal to 35% of monomer units derived from a monomer of formula (I);
   c) of a mole proportion of greater than or equal to 0.005% and less than or equal to 5 mol % of monomer units derived from the compound of formula (II); and
   d) of a mole proportion of greater than or equal to 0.005% and less than or equal to 5 mol % of monomer units derived from at least one diethylenic or polyethylenic crosslinking monomer.

9. The crosslinked anionic polyelectrolyte as defined in claim 1, derived from the polymerization, per 100 mol %:
   a) of a mole proportion of greater than or equal to 60% and less than or equal to 90% of monomer units derived from 2-methyl-2-[(1-oxo-2-propenyl)amino]-1-propanesulfonic acid, which is free, partially salified or totally salified in sodium salt or ammonium salt form;
   b) of a mole proportion of greater than or equal to 9% and less than or equal to 35% of monomer units derived from 2,2,2-trifluoroethyl methacrylate;
   c) of a mole proportion of greater than or equal to 0.5 mol % and less than or equal to 2 mol % of monomer units derived from stearyl methacrylate, and
   d) of a mole proportion of greater than or equal to 0.5% and less than or equal to 3% of trimethylol triacrylate.

10. The anionic polyelectrolyte as defined in claim 1, comprising a mole proportion of greater than 0% and less than or equal to 5% of at least one diethylenic or polyethylenic crosslinking monomer.

11. The anionic polyelectrolyte as defined in claim 10, wherein said at least one diethylenic or polyethylenic crosslinking monomer is methylenebis(acrylamide) or trimethylolpropane propanetriacrylate.

12. A cosmetic, dermopharmaceutical or pharmaceutical topical composition comprising the anionic polyelectrolyte as defined in claim 1, as a thickener, a stabilizer and/or an emulsifier.

13. A cosmetic topical composition, comprising from 1% to 5% by mass of the anionic polyelectrolyte as defined in claim 1 and from 1% to 10% by mass of glycerol.

14. The composition as defined in claim 13, wherein the composition is free of silicone oil.

15. A process for preparing the polyelectrolyte as defined in claim 1, comprising:
   (a) preparing a reaction mixture comprising, in the desired mole proportions and in a solvent (S), the monomer(s) comprising a free, partially salified or totally salified strong acid function, the monomer(s) of formula (I), the monomer units derived from the compound of formula (II); and optionally, the diethylenic or polyethylenic crosslinking monomer(s), said solvent (S) being:
either a ketone of formula (III):

$$(R_5)(R_6)C=O \quad (III),$$

in which $R_5$ and $R_6$, which may be identical or different, represent, independently of each other, a methyl radical, an ethyl radical, an isopropyl radical or an isobutyl radical;

or a mixture comprising, per 100 mol %: water in a proportion of greater than 0 mol % and less than or equal to 25 mol %; and a ketone of formula (III) as defined above, in a proportion of greater than or equal to 75 mol % and less than 100%;

or tert-butanol;

(b) initiating the polymerization reaction by introducing into said reaction mixture prepared in step (a), a free-radical initiator, and allowing the reaction to proceed until finished, to obtain a precipitate of said polyelectrolyte, (c) optionally, isolating said precipitate obtained in step (b) by separation from said solvent (S), and (d) optionally, drying said precipitate resulting from step (c).

16. The process as defined in claim 15, comprising:

(c) isolating said precipitate obtained in step (b) by separation from said solvent (S), and (d) drying said precipitate resulting from step (c).

* * * * *